United States Patent
Adrian et al.

[11] Patent Number: 5,925,055
[45] Date of Patent: Jul. 20, 1999

[54] MULTIMODAL ROTARY ABRASION AND ACOUSTIC ABLATION CATHETER

[75] Inventors: Sorin Adrian, Penn Valley; Paul Walinsky, Wyndmoor, both of Pa.

[73] Assignee: Medelex, Inc, Penn Valley, Pa.

[21] Appl. No.: 08/933,499

[22] Filed: Sep. 18, 1997

Related U.S. Application Data

[60] Provisional application No. 60/050,569, Jun. 23, 1997.

[51] Int. Cl.$^6$ .................................................. A61B 17/22
[52] U.S. Cl. .......................... 606/159; 606/169; 606/170; 606/171; 606/178; 604/22
[58] Field of Search .................................... 606/159, 169, 606/170–171, 178, 80, 180; 604/22; 601/2

[56] References Cited

U.S. PATENT DOCUMENTS 5,423,797  6/1995  Adrian et al. ............................... 606/1
5,569,179  10/1996  Adrian ....................................... 604/22

Primary Examiner—Michael Buiz
Assistant Examiner—Lien Ngo
Attorney, Agent, or Firm—William H. Meise

[57] ABSTRACT

An ablation and cutting catheter (10), which may be used for angioplasty, includes a rotary shaft (20) adapted to be driven by a rotary motor (22). The shaft (20) is free for rotation and for some axial motion. The shaft (20) is coupled to a rotational-to-axial motion converter (FIGS. 2*a*, 2*b*, 2*c*; 3*a*, 3*b*, 3*c*) which is affixed to the shaft. The converter moves axially in response to rotation of the shaft, and also rotates. The axial motion is converted into acoustic energy for ablation, and the rotation can be used with a cutting tool for cutting. A guide-wire lumen extds through the shaft and the cutter/acoustic applicator head, for accepting a guide-wire for guiding the catheter.

20 Claims, 8 Drawing Sheets

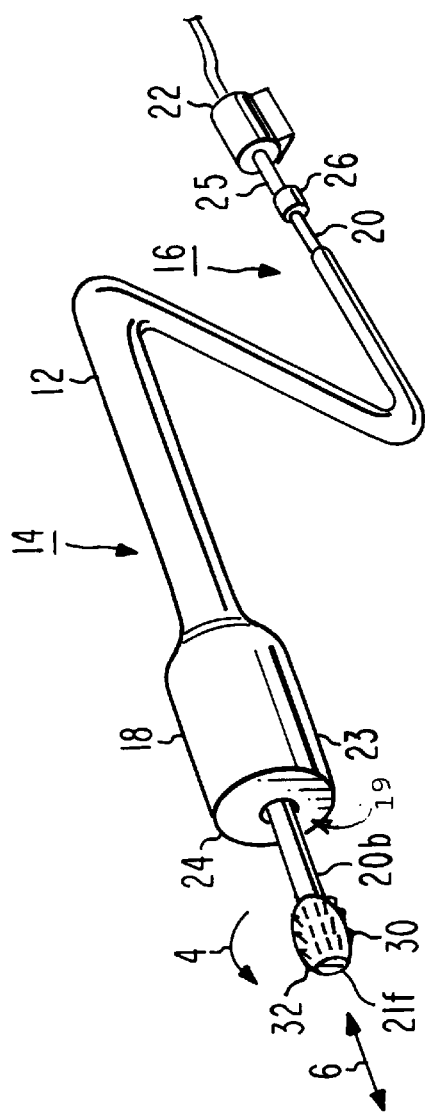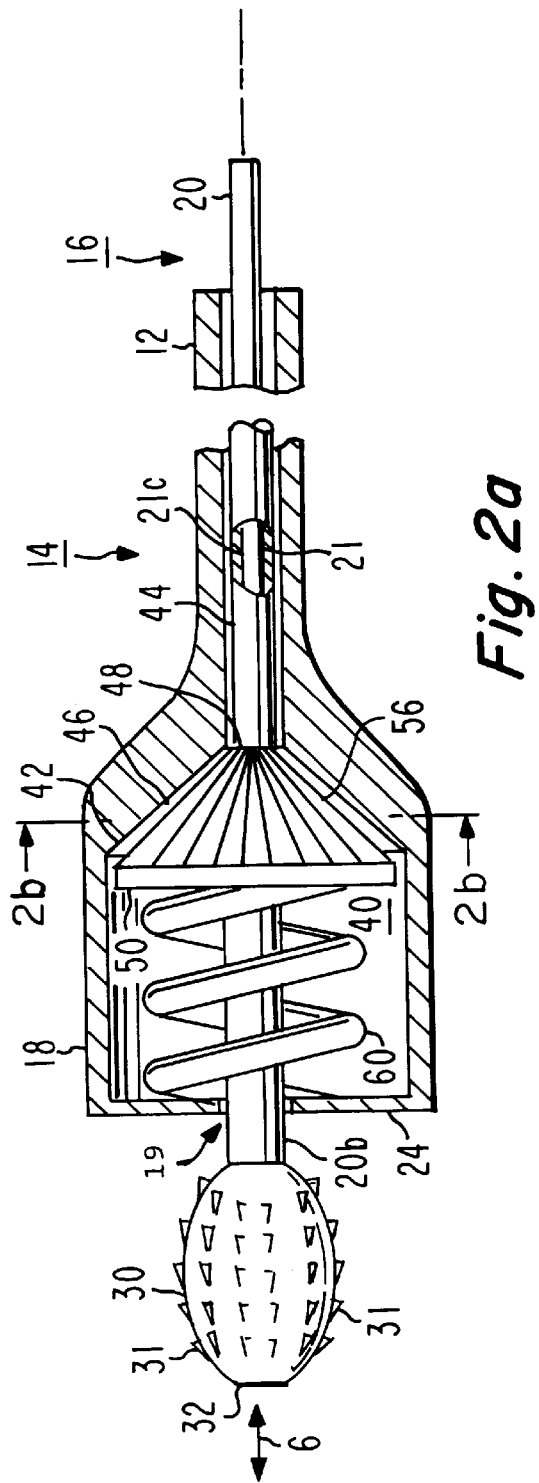

MULTIMODAL ROTARY ABRASION AND ACOUSTIC ABLATION CATHETER

This is a continuation of U.S. Provisional Patent Application Ser. No. 60/050,569, filed Jun. 23, 1997, and entitled SIMPLIFIED ACOUSTIC ABLATION CATHETER.

FIELD OF THE INVENTION

This invention relates to acoustic ablation catheters, and more particularly to such catheters which are driven by a rotational shaft.

BACKGROUND OF THE INVENTION

An ultrasound or acoustic angioplasty catheter as described in U.S. Pat. No. 5,423,797, issued Jun. 13. 1995 in the name of Adrian et al., reduces transmission losses, and reduces unwanted heating of the transmission member, by adapting the catheter to be driven by a rotary motor, and by generating the acoustic energy within the body, rather than, as in the prior art, generating the acoustic energy without or outside the body and coupling it into the body by means of a transmission member such as a longitudinally excited wire. The catheter as described therein includes an elongated body defining a distal end and a proximal end, and a shaft extending longitudinally through the body. The shaft includes a drive coupling arrangement near the proximal end of the catheter, which is adapted to be coupled to the rotary motor, for causing the shaft to be driven in a continuous-rotation manner. A rotary-to-axial motion converter is coupled to the shaft near the distal end of the catheter, for converting the rotary motion into axial motion in the form of acoustic energy. In a particularly advantageous embodiment, the rotary-to-axial motion converter includes a swash plate coupled to the shaft for being rotationally driven thereby. The swash plate defines a surface which, at a reference point which is angularly fixed relative to the catheter body, moves axially in response to the rotary motion of the swash plate. In another embodiment, the follower engages a sinusoidal groove in the periphery of the drive coupling arrangement.

Another acoustic arrangement is described in U.S. Pat. No. 5,569,179, issued Oct. 29, 1996 in the name of Adrian, in which the catheter includes an elongated shaft defining a distal end and a proximal end. The proximal end of the shaft includes a coupling arrangement for coupling to a rotary drive such as an external rotary motor. The catheter also includes a rotary-to-axial motion converter coupled to the distal end of the shaft. The motion converter includes at least a first magnetic pole mechanically coupled to the distal end of the shaft for being rotated thereby along an arc. The motion converter also includes a nonrotating reciprocating device or follower, and at least a second magnetic pole which is located so as to come within the magnetic influence of the first magnetic pole during each the rotation of the shaft. During each rotation, the two magnetic poles attract or repel, for causing reciprocating axial motion of the reciprocating device relative to the distal end of the shaft. This motion generates acoustic energy in the fluid medium located at the distal end of the catheter. An advantage of some of the embodiments over some of the swash-plate embodiments of the prior art is that a spring arrangement is not needed to return the follower after an excursion in one direction, which reduces heating losses in the spring.

Yet another acoustic catheter arrangement having a low-friction drive is described in U.S. Pat. No. 5,593,415, issued Jan. 14, 1997 in the name of Adrian., in which the rotary-to-axial motion converter includes a rotary portion coupled to the shaft for being driven in a rotary manner thereby, and the rotary portion of the rotary-to-axial motion converter defines a bearing surface which includes portions which, relative to a point fixed on the body of the catheter, move axially in response to rotation of the rotary portion. The axial motion reciprocates in response to the rotation of the shaft. The catheter also includes a magnetic arrangement coupled to the rotary portion of the rotary-to-axial motion converter and to the follower, for generating a magnetic force between the bearing surface of the rotary portion of the rotary-to-axial motion converter and the bearing surface of the follower, which force tends to reduce friction between the bearing surfaces of the rotary portion and the follower portion of the rotary-to-axial motion converter.

An easily fabricated rotary acoustic ablation catheter is described in U.S. patent application Ser. No. 08/829,052, filed Mar. 31, 1997 in the name of Adrian, in which the rotary-to-axial motion converter of the catheter further comprises a rotary driver coupled to the shaft, for being driven in a rotary manner thereby in response to rotation of the shaft. The rotary driver includes a cylindrical shell with an outer surface having the general outer shape of a right circular cylinder defining distal and proximal ends. The cylindrical shell also defines an inner surface with a guide path which is circumferentially continuous about the circumference of the inner surface of the shell. The guide path has portions which lie closer to the distal end of the cylindrical shell and other portions which lie closer to the proximal end of the shell. The rotary-to-axial motion converter of the catheter also includes a follower coupled to the guide path. The follower is fixed against rotation, so it cannot rotate with the rotary driver. The follower is mechanically coupled to the guide path, for being reciprocally driven in an axial manner in response to rotation of the shaft, shell, and guide path. This arrangement has the advantage of minimizing the diameter of the rotary-to-axial-motion converter.

Improved rotationally driven acoustic ablation catheters are desired.

SUMMARY OF THE INVENTION

An acoustic ablation catheter according to the invention is adapted for being driven by a rotary motor. The catheter includes an elongated housing defining a distal end and a proximal end, and a shaft extending at least part-way through the housing. A guide wire lumen may be present in the center of the shaft to accommodate a guide wire for control of the directional advancement of the catheter. The shaft is free for rotation and axial motion within the housing. A rotary coupler is coupled to a proximal end of the shaft, for coupling the shaft to the rotary motor for being driven thereby. An axial motion imparting arrangement located near the distal end of the housing, and coupled to the shaft, causes the shaft to experience axial motion in response to the rotation. An acoustic transducer is coupled to a distal end of the shaft for rotational and axial motion in response to the rotation and axial motion of the shaft. The acoustic transducer is adapted for transferring the axial motion to a biological material, which may be fluid, flesh-like, or solid, or an intermixture of both.

In a particular embodiment of the invention, the axial motion imparting arrangement includes a toothed surface associated with the shaft, bearing on an irregular surface of the housing, together with a spring arrangement bearing on a portion of the housing, for urging the toothed surface toward the irregular surface, which results in rotational motion of the toothed surface against the irregular surface, which in turn results in the axial motion of at least a portion of the shaft near the distal end of the catheter.

In another embodiment of the invention, the axial motion imparting arrangement includes a sinusoidal track associated with one of the shaft and the housing, and a track following arrangement associated with the other one of the shaft and the housing, for imparting sinusoidal axial motion to the shaft. In other embodiments of the invention, the track is not sinusoidal, but instead has a form, such as trapezoidal, selected to impart a harmonic content to the acoustic wave.

In yet another embodiment of the invention, the axial motion imparting arrangement includes magnets associated with one of the shaft and the housing, and magnetically influenceable material associated with the other one of the shaft and housing. The magnetically influenceable material may be a magnetic or diamagnetic material, or it may be another magnet arrangement.

BRIEF DESCRIPTION OF THE DRAWING

FIG. 1 is a simplified perspective or isometric view of a catheter according to an aspect of the invention, and its rotary drive motor;

FIG. 2a is a cross-sectional view of the embodiment of FIG. 1 illustrating a first type of rotary-to-axial-motion converter including a serrated conical acoustic transducer arrangement and a position restoring spring.

FIG. 3c is a developed view of a trench or guide path about the interior wall of the housing of FIG. 3a;

DESCRIPTION OF THE INVENTION

Figure 2B:
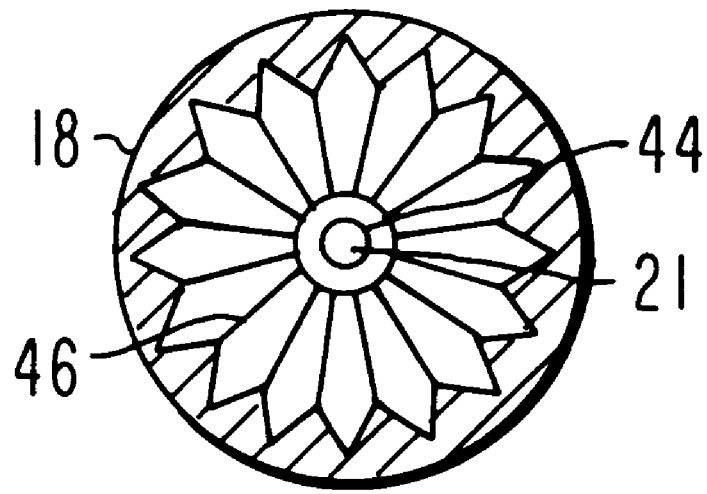
FIG. 2b is a cross-sectional view of the structure of the arrangement of FIG. 2a, which illustrates details of the serrated surface of a conical portion of the housing of FIG. 2a in the absence of other elements.

In FIG. 1, a catheter 10 according to an aspect of the invention includes a flexible catheter body 12, defining a distal end 14 and a proximal end 16. The distal end 14 of catheter body 12 is enlarged into a casing 18. A flexible rotational drive shaft 20 extends through body 12, and extends therefrom at proximal end 16, and also extends through an aperture 22 in the end wall 24 of casing 18. As illustrated in FIG. 1, the shaft 20 is connected to, or terminates in, an applicator head 30. As described in more detail below, the applicator head 30 moves both rotationally and axially. A rotary motor 22 has a shaft 25. Shaft 20 of catheter 10 has a coupler 26, adapted for connection to shaft 25 of motor 22.

FIG. 2a is a simplified cross-sectional view of the distal end of the arrangement of FIG. 1, illustrating a first type of rotary-to-axial-motion converter. In FIG. 2a, housing 18 is seen to include a cavity 40 with a conical proximal wall 42, which merges into an elongated lumen 44. Lumen 44 is dimensioned to be larger than the diameter of shaft 20. Shaft 20 is not necessarily centered in the lumen 44, but is retained in a generally centered condition by the presence of lubricant, not illustrated. A cut-away section 21c of shaft 20 reveals a guide wire lumen 21 in the center of shaft 20, which extends through the shaft, and continues through applicator head or burr 30 to exit in a frenulum 21f, to accept a guide wire (not illustrated in FIG. 2a) to aid in maintaining the shaft 20 centered in the lumen 44, and to guide the catheter in a conventional guide-wire manner. Conical proximal wall or surface 42 has a plurality of elongated serrations or indentations 46, more readily seen in the cross-section of FIG. 2b. While a large number of serrations is illustrated, the number may be as few as two, equally spaced about the periphery, or possibly even one. The axial depth or dimensions of the serrations are determined, in part, by the desired axial excursion.

As illustrated in FIG. 2a, shaft 20 is connected at a junction 48 to a rotationally free conical element 50. The conical face of conical element 50 carries elongated serrations or indentations 56, more readily seen in the end-on view of element 50 of FIG. 2c. As in the case of the number of serrations in catheter wall or surface 42, the number of serrations in conical element 50 may be fewer than illustrated. It will be clear to those skilled in the art that the frequency multiplication of the acoustic energy relative to the shaft rotation will depend on the interaction of the number of serrations on the conical element 50 and on the body wall 42. A further stub, segment, or portion 20b of shaft 20 extends distally beyond conical element 50, and extends through aperture 22 in end wall 24 of housing 18. A burr or applicator with a flat end 32 is illustrated as being affixed to, or a part of, the distal end of shaft 20b. An energy restoring element, illustrated in FIG. 2a as a helical spring 60, bears against the inner surface of end wall 24 of housing 18, and also bears against the flat distal end of conical element 50.

Figure 2C:
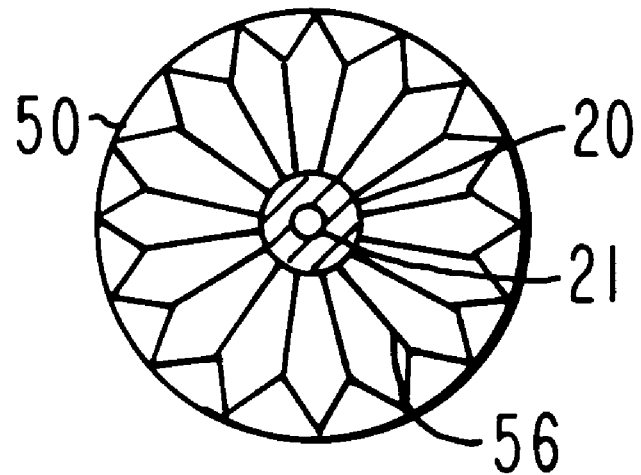
FIG. 2c is an end view of a conical element with serrations which interact with the serrations of FIG. 2b to cause axial acoustic motion.

In the arrangement of FIGS. 2a, 2b, and 2c, the spring 60 urges the serrated conical surface of element 50 into contact with the serrated conical surface 42. When the shaft rotates under the impetus of torque applied from motor 22, conical element 50 rotates, and its serrations interact with the serrations of conical surface 42 in a manner which results in axial motion of conical element 50, and of shaft 20 and shaft segment 20b. Thus, in normal operation, shaft segment 20b rotates and vibrates axially. Burr 30, affixed to the end of shaft segment 20b, is the element which both generates acoustic energy by vibrating axially in the direction indicated by double-headed arrow 6, and cuts by rotation (4) of the cutting surfaces 31 of burr 30 against the matter to be removed. It should particularly be noted that the burr is not needed, but the axially vibrating conical element 50 itself produces acoustic energy, which may be used directly, if desired, by coupling the acoustic energy from the housing to the region to be ablated. Thus, the structure as so far described, in the absence of the burr, is sufficient to produce a simplified acoustic ablation catheter, in which the simplification relative to the abovedescribed Adrian et al., and Adrian patents, and Adrian application, lies in the lack of a second element which is retained against rotational motion, and which moves only axially. The conical element 50 of the arrangement of FIGS. 2a, 2b, and 2c moves both rotationally and axially, and thus itself accomplishes the axial motion performed in the abovementioned prior art by two separate elements.

In operation of the arrangement of FIGS. 2a, 2b, and 2c, the burr 30 moves in an axial direction, to thereby produce acoustic energy as described generally in the abovementioned Adrian et al. and Adrian patents, and in the Adrian application. The acoustic energy can be used to tend to sonicate plaque into small particles. Further, the burr 30 rotates, thereby allowing its cutting surfaces 31 to be used to abrade into small particles not otherwise removed by the acoustic energy. The central portion of the burr 30, which is illustrated as being flat, generates an acoustic field which tends to have its maximum intensity in an axial direction, so that plaque in a peripheral portion of the acoustic field may not be removed as readily; the abrasive or cutting action of the burr occurs where the rotational motion is greatest, which is around the periphery of the burr. Consequently, the rotational cutting or abrading action of the burr complements the axial sonification action of the acoustic portion of the energy.

While the burr is illustrated as having a flat end for generating axially-directed acoustic energy, it may have many different configurations for acoustic focussing or for dispersion of the acoustic wave.

Figure 2D:
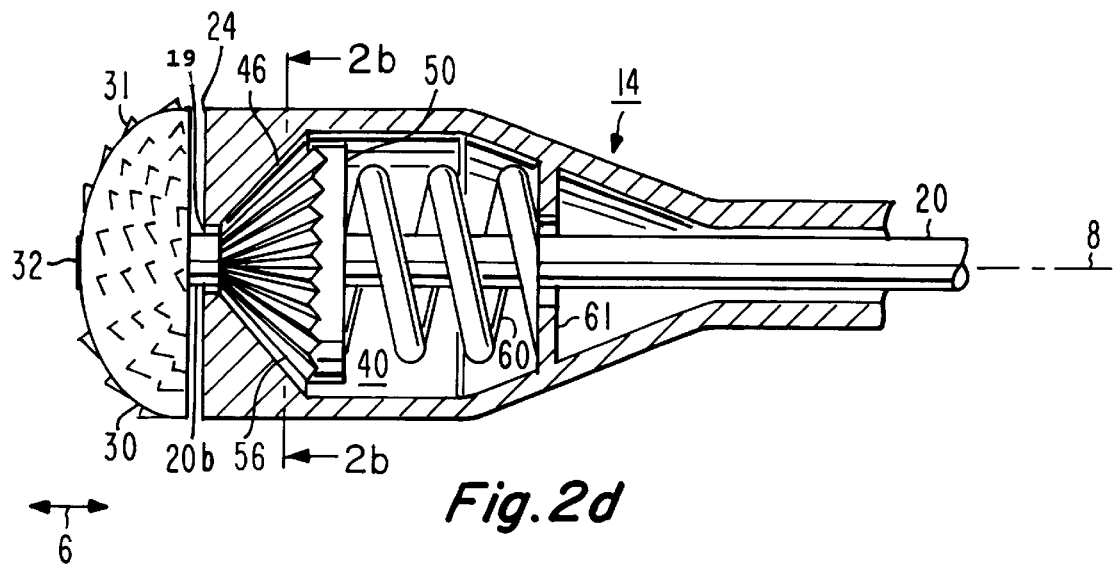
FIG. 2d is a cross-section of a catheter similar to that of FIG. 2a, illustrating a reversal of the positions of the conical acoustic transducer and the position-restoring spring.

FIG. 2d is a simplified cross-sectional view of another embodiment of the invention, in which elements corresponding, at least in principle, to those of FIG. 2a, are designated by like reference numerals. In FIG. 2d, the conical acoustic generating surfaces are distal relative tho those of FIG. 2a, and spring 60 bears at its rear or its proximal portion against a wall 61, and pushes the disk-like element 50 forward into contact with the serrations 46 in the housing. The serrations in the housing of FIG. 2d are identical to those illustrated in FIG. 2b, and the disk-like element is the same as that illustrated in FIG. 2c. The arrangement of FIG. 2d is the "reverse" of that of FIG. 2a. The arrangement of FIG. 2d may have more or less serrations on its acoustic transducer, as described in conjunction with FIGS. 2a, 2b, and 2c.

Figure 2E:
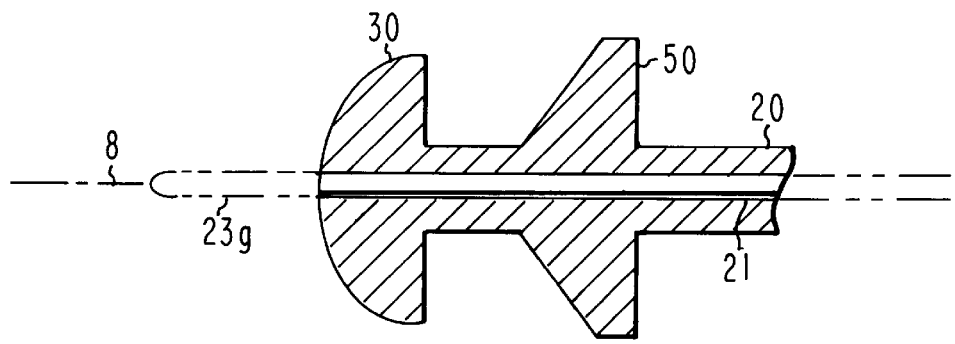
FIG. 2e is a cross-sectional view of a distal portion of the drive shaft of the arrangement of FIG. 2d, illustrating a guide-wire lumen.

According to an aspect of the invention, a guide wire may be provided for use with catheters according to the invention. The guide wire provides the usual function of guiding the distal end of the catheter, and also may aid in maintaining the concentricity of the drive shaft 20 within the body 12 of the catheter 10. FIG. 2e illustrates a cross-section of a distal portion of a drive shaft 20, with its disk-like element 50 and a burr 30, with a guide-wire lumen 21 penetrating axially therethrough. The guide-wire itself is illustrated as 23. Of course, such a lumen and guide-wire may also be used in conjunction with a catheter configured as in FIG. 2a.

Figure 2G:
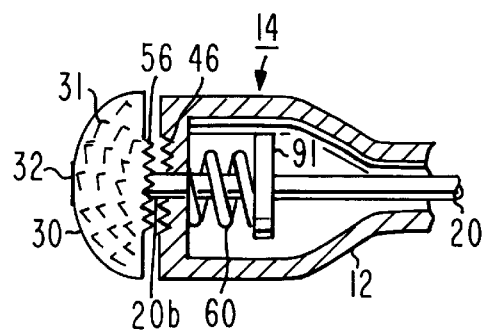
FIG. 2g illustrates yet another embodiment of a catheter according to the invention, in which the serrated surface of the acoustic transducer is integral with the rear surface of the burr.
Figure 2F:
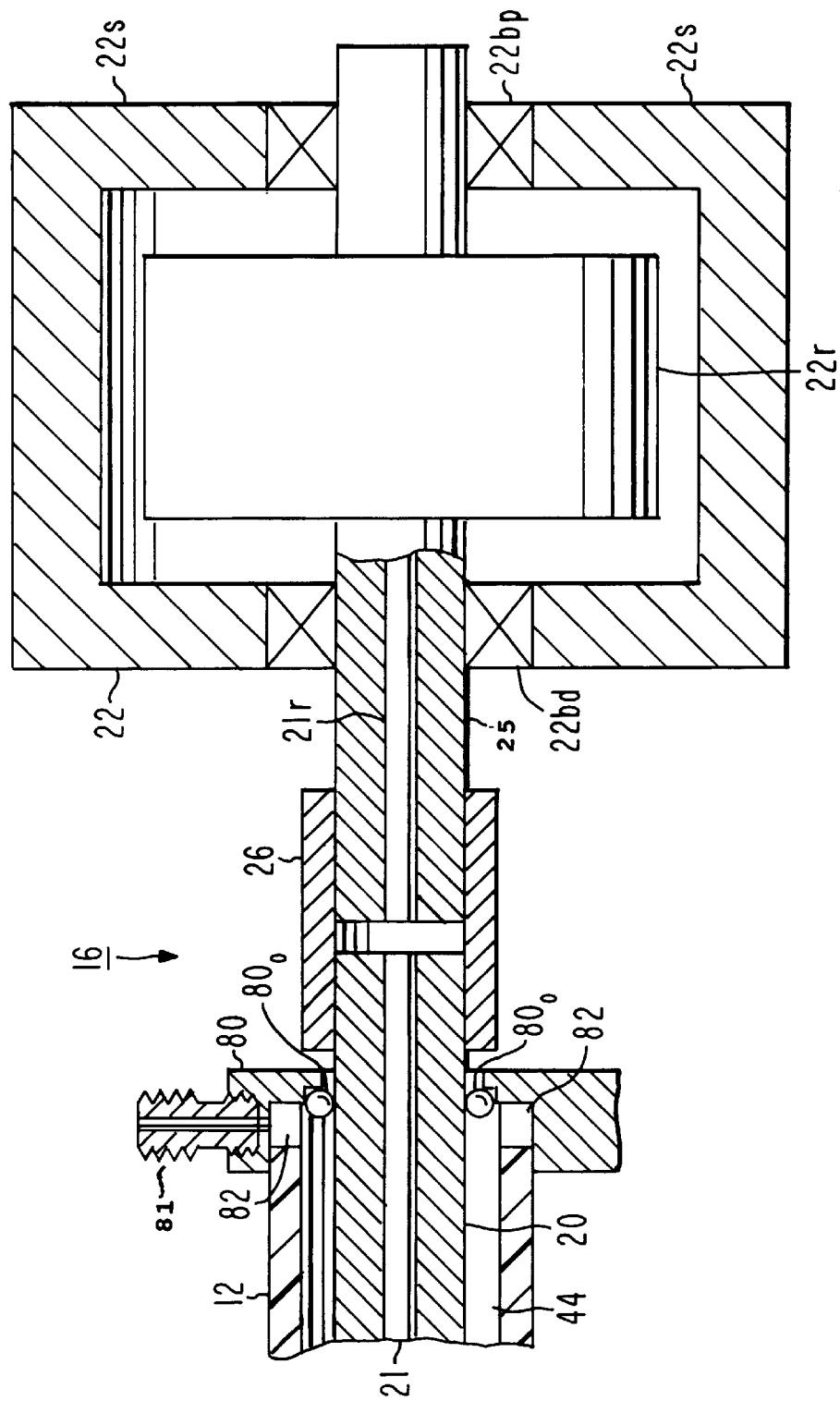
FIG. 2f is a cross-section of a distal portion of the catheters of FIGS. 2a or 2d, illustrating where the guide wire is introduced, and a method for lubricating and cooling the moving parts of the catheters.

The guide-wire lumen extends completely through the center of the shaft 20, and also extends through the coupler 26 and through the center of the shaft 25 of drive motor 22 of FIG. 1, as illustrated in more detail in the arrangement of FIG. 2f. In FIG. 2f, the proximal end 16 of the catheter body 12 is connected to a lubricant ingress fitting 80. Fitting 80 is affixed to the end of the catheter body 12 with O-rings 80$_o$, and includes a tubing fitting 81 which provides lubricant ingress from the tube (not illustrated) to an annular lubricant chamber 82. Chamber 82 allows lubricant/coolant to enter the proximal end of the catheter, and to flow under pressure toward the distal end of the catheter, to lubricate and cool the moving parts, and to aid in centering the shaft 20 within the outer body 12. The lubricant/cooling liquid entering the proximal end of the catheter flows under pressure to the distal tip of the catheter, where it is released through lateral openings. The lubricant is preferably biocompatible, and saline solution mixed with 10% INTRALIPID, manufactured by Kabi Pharmacia may be used. The lubricant may be applied under a pressure of, for example, 20 to 50 PSI, although 10 to 200 PSI appear suitable. The lubricant/coolant flows through the lumen 44, in the space between the sides body 12 and the drive shaft 20, and exits from the distal end of the catheter. As also illustrated in FIG. 2f, shaft coupling arrangement 26 is hollow, and the shaft 25 of motor 22 defines a lumen, which allows a guide wire to be inserted at port 21r at the rear of the motor, all the way through to the distal end of the burr; the biocompatible nature of the lubricant/coolant, and the relatively small volume of flow, result in no adverse effect on the patient. For completeness, motor 22 is illustrated as including distal and proximal bearings 22bd and 22bp, respectively, a rotor 22r affixed to motor shaft 21, and an associated stator 22s.

While the rotary-to-acoustic energy converters (the interacting serrated portions 46, 56) as illustrated in FIGS. 2a, 2b, 2c, and 2d are conical, in order to aid in centering the rotating structures within the housing, they could be of mating curved configurations, or they could be flat, if the centering of the rotating parts is not of great concern. FIG. 2g illustrates a preferred embodiment of a catheter according to the invention, in which the serrated or toothed surface 46 is located on the front surface of end wall 24 of the catheter body 12, and the corresponding serrated portion 56 is located on the rear surface of the burr or acoustic transducer 30. Naturally, the embodiment of FIG. 2g may include a guide-wire lumen, as described in conjunction with FIG. 2e.

Figure 3A:
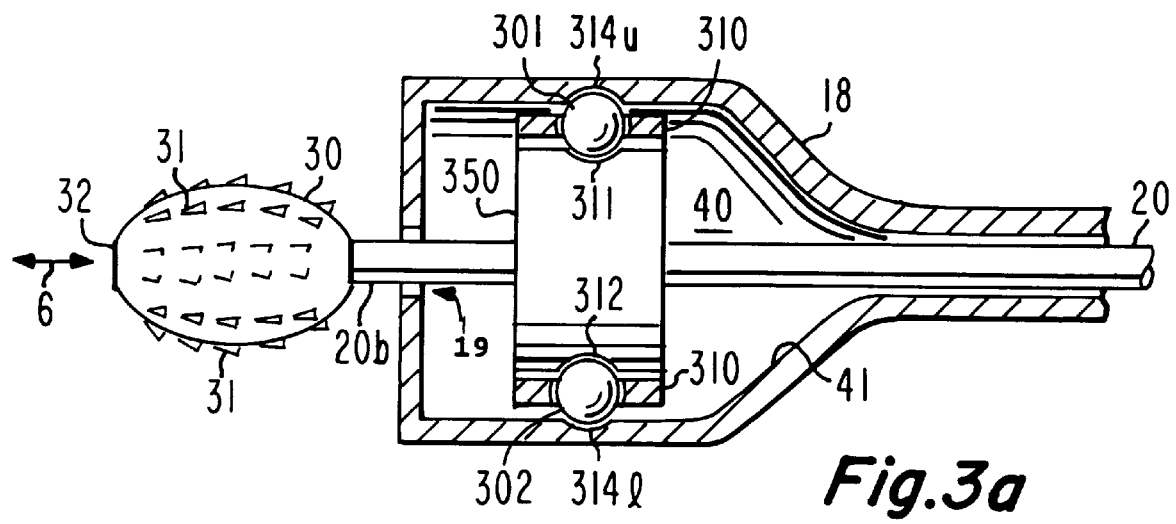
FIG. 3a is a cross-sectional view of the embodiment of FIG. 1, illustrating a second type of rotary-to-axial-motion converter.

FIG. 3a is a simplified cross-sectional view of the structure of FIG. 1, illustrating another type of combination axial/rotary motion driver which requires no restoring spring. In FIG. 3a, elements corresponding to those of FIGS. 1 and 2a are designated by like reference numerals. The axial motion converter portion of the arrangement of FIG. 3a includes a disk-like element 350, which is supported by ball bearings, two of which are illustrated as 301 and 302. An annular retainer or cage 310 prevents unwanted motion of the ball bearings. Disk-like element 350 has a circular socket 311 formed in its peripheral surface in which ball bearing 301 is retained, and a similar circular socket 312 retains ball bearing 302. Thus, when disk-like element 350 rotates, it carries the ball bearings 301, 302 in a circular path near its periphery. While the ball bearing retaining cage will tend to be held in position by the balls 301, 302 . . . , it is desirable that the ball bearing retaining cage 310 be fixed in position relative to the rotating disk-like element 350.

Figure 3B:
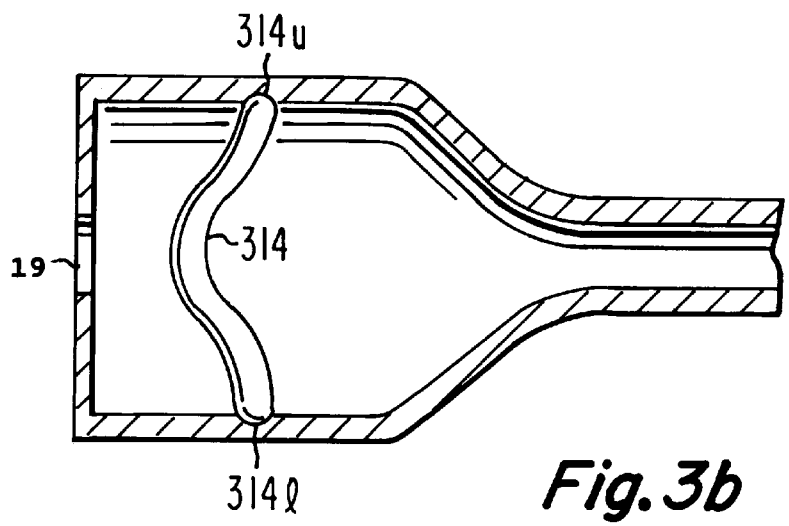
FIG. 3b is a view of the interior of the housing of the arrangement of FIG. 3a in the absence of other elements.
Figure 3C:
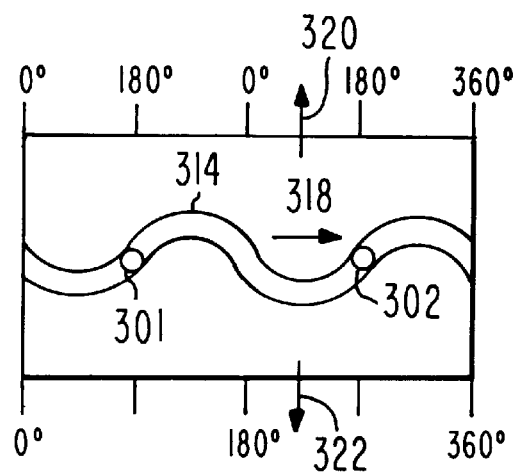

FIG. 3b is a cross-sectional view of the housing 18 of FIG. 3a, without the shaft 20, shaft segment 20b, disk-like element 350, ball bearings 301, 302, or retainer 310. The angles ranging from 0° to 360° along the bottom of FIG. 3c represent physical angle around the periphery of the disk-like element 350. An elongated, generally sinuous trough illustrated as 314 extends around the inner surface 41 of the cavity 40 of housing 18. The sinuous path is a guide path for the ball bearings 301, 302. FIG. 3c is a developed view of the entirety of the interior surface 41 of housing 18, illustrating a sinusoidal overall shape of trough 314, with two cycles of sinusoid occurring about the inner periphery of housing 18. The angles associated with the two cycles of sinusoidal trough are indicated along the top of FIG. 3c. It will be noted that two 0°-to-360° cycles of sinusoid occur in 360 physical degrees. Instantaneous locations of the two ball bearings 301 and 302 are shown, and their direction of motion in response to rotation of the disk-like element 350 is indicated by arrow 318. As a result of the rotation, the ball bearings move axially as they follow along the sinuous trough 314. It will be appreciated that while only one instantaneous position is shown, the ball bearings move along the sinusoidal path 314, moving axially, which in FIG. 3c is in the direction of up and down arrows 320 and 322, respectively.

Figure 4A:
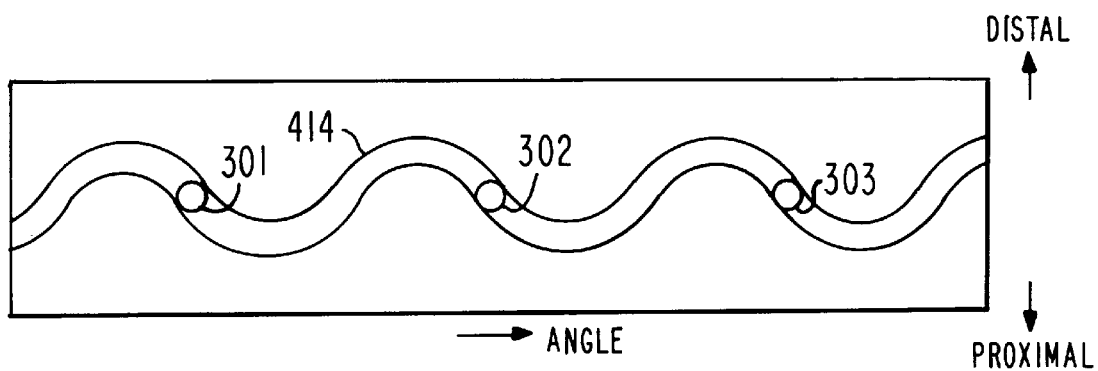
FIG. 4a is a developed view of a trough around the interior of the wall of a catheter illustrating three sinusoids around the periphery, and also illustrating the locations of the ball bearings at an instant in time.
Figure 4B:
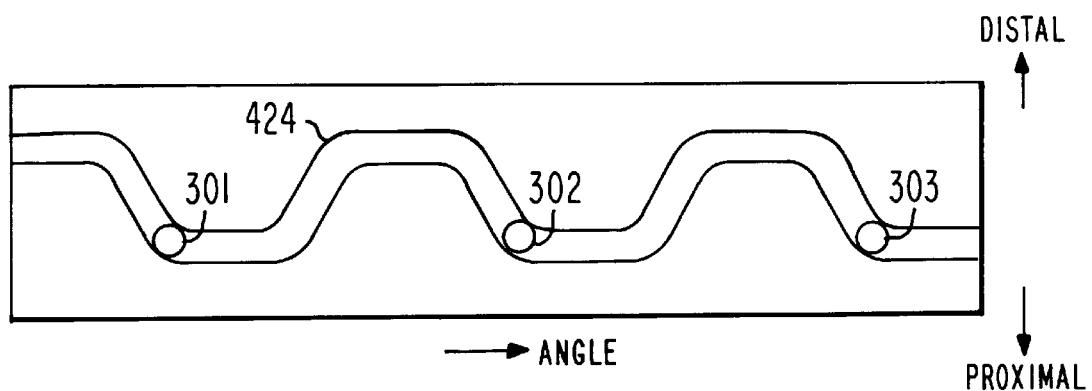
FIG. 4b is a similar developed view illustrating a trapezoidally-shaped trough.

It is possible to add more ball bearings around the periphery of the disk-like element 350. This requires adding one more cycle or period of sinusoidal trough around the inner periphery of housing 18 for each ball to be added. For example, FIG. 4a is a developed view of the interior of a housing such as 18, which has three complete cycles of sinusoidal trough 414 around its periphery, and accommodates three ball bearings designated 301, 302, and 303. Naturally, a trough defining a four-cycle sinusoid will accommodate four balls, and so forth. FIG. 4b is a similar developed view, which illustrates a trough having three squared-off or trapezoidal-shaped cycles rather than sinusoidal, for enhancing the harmonic content of the acoustic wave. The acoustic frequency resulting from rotation of the shaft will tend to be higher when the track defines a larger number of cycles; if there is but one cyclical axial motion for each rotation, the sonic frequency will be equal to the number of shaft rotations per second, while if there are two, three, or four cycles in the trough, the acoustic frequency will be twice, thrice, or four times the rotations per second. Other shapes for adjusting the harmonic content will be apparent to those skilled in the art.

Rotational motion of the shaft 20 of FIG. 3a rotates disk-like element 350, and the ball bearings 301, 302, . . . are carried along with the rotating periphery of element 350 because each ball sits in a semispherical depression, such as 311, 312 of FIG. 3a. For this purpose, a semisphere is a portion of a sphere which is less than a hemisphere. As the ball bearings rotate with the disk-like element 350, they are constrained to follow trough 314, and the ball bearings therefore move back and forth in an axial direction in response to the rotation. If there are three complete cycles or periods of sinusoidal trough around the inner periphery of housing 18, each ball must make three back-and-forth axial excursions for each rotation of disk-like element 350. This results in axial motion with three excursions per rotation, which means that there is an effective frequency multiplication, creating an axial or acoustic wave with a frequency which is an integer multiple of the rotational frequency. The burr 30 of the arrangement of FIG. 3a rotates and moves axially just as in the arrangement of FIG. 2a, and may be used in the same fashion.

Figure 5A:
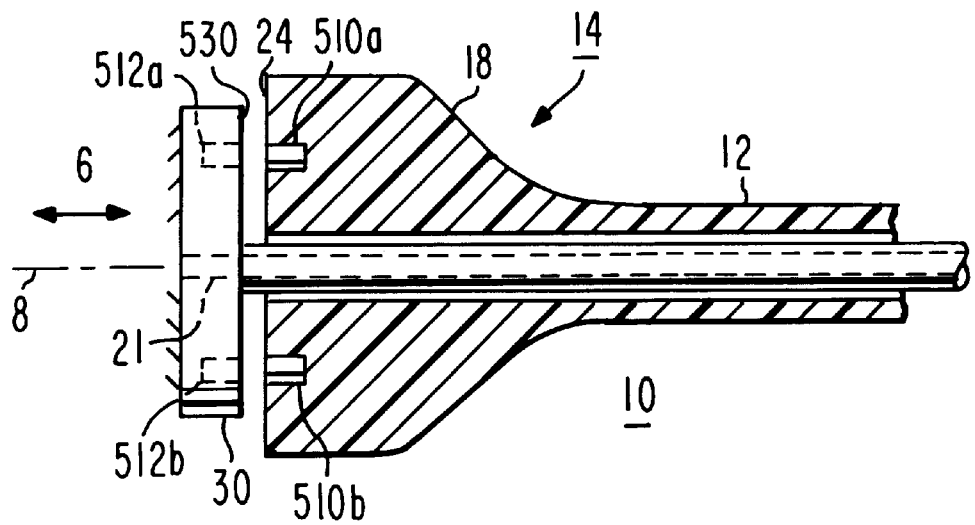
FIG. 5a is a cross-section of an acoustic catheter according to the invention, in which magnets provide the rotary-to-axial motion conversion.

FIG. 5a is a cross-section of another embodiment of the invention, in which a plurality of individual magnets are associated with the rotating and fixed portions of the catheter, for, by mutual repulsion andor attraction, causing forces which, in turn, result in axial motion, thus converting rotational motion into axial motion or sonification. In FIG. 5a, and in exploded view 5b, elements corresponding to those of FIGS. 1, 2a, and 2d are designated by like reference numerals. While it would be possible to add the magnets to a portion of the catheter such as disk-like portion 50 of FIGS. 2a and 2d, the presence of the frontal end wall 24 of body 12 of the catheter, and the flat rear portion of burr 30, provides an alternative location for the magnets, which is better in that there is no need for the disk-like element, and the moving mass is reduced.

Figure 5B:
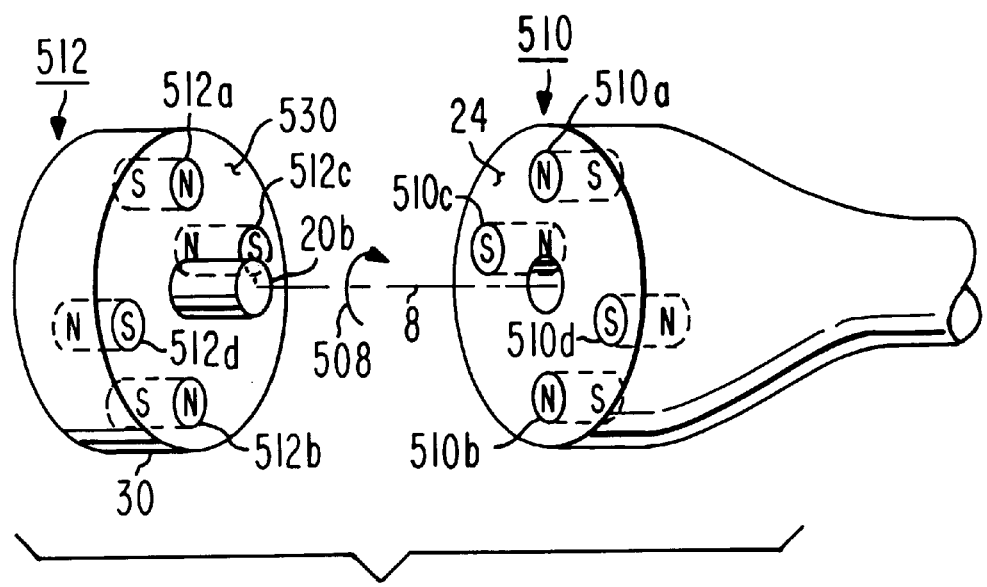
FIG. 5b is an exploded view of portions of the catheter of FIG. 5a, illustrating details of the drive magnet location and poling.

In FIGS. 5a and 5b, the burr/acoustic transducer element is designated 30, although it could also be designated 30/50, to indicate its dual use. The end wall 24 of the body 12 of catheter 10 of FIGS. 5a and 5b bears an array 510 of magnets designated 510a, 510b, 510c, and 510d, each of which has a north (N) pole and a south (S) pole. The magnets are physically embedded into the material of the catheter body. Diametrically oppositely-located magnets 510a and 510b have their N poles adjacent the front face of end wall 24, while diametrically-opposed magnets 510c and 510d, located circumferentially between magnets 510a and 510b, have their S poles adjacent the front face of end wall 24. Similarly, the rear face 530 of burr 30 of FIGS. 5a and 5b bears a set 512 of four imbedded magnets designated 512a, 512b, 512c, and 512d, each of which has a north (N) pole and a south (S) pole. Oppositely located magnets 512a and 512b have their N poles adjacent the rear face 530, while magnets 512c and 512d, located between magnets 512a and 512b, have their S poles adjacent the rear face 530.

In operation of the arrangement of FIGS. 5a and 5b, rotation of the shaft causes the burr 30 to rotate, and its rear surface 530 also rotates near the surface of end wall 24 of the catheter body. As the burr rotates, its magnet set periodically comes into alignment with the magnet set of the body. Thus, at the rotational position illustrated in FIGS. 5a and 5b, magnets 510a, 510b, 510c, and 510d are in mutual interaction with magnets 512a, 512b, 512c, and 512d, respectively, and all of the magnet pairs are poled for mutual repulsion. Consequently, in the illustrated position, the burr 30 is repelled away from the body 12 of the catheter 10, tending to cause motion in a distal direction. One-quarter rotation later, in the direction indicated by arrow 508 of FIG. 5b, the N magnetic pole of magnet 512a aligns with the S pole of magnet 510c, the S magnetic pole of magnet 512c aligns with the N pole of magnet 510b, the N magnetic pole of magnet 512b aligns with the S pole of magnet 510d, and the S magnetic pole of magnet 512d aligns with the N pole of magnet 510a. In this quarter-rotated position, the magnets attract, causing the burr 30 to be attracted toward the catheter body 12, resulting in motion in a proximal direction. One-quarter rotation later, which is one-half rotation from the illustrated position, the magnets are again aligned for mutual repulsion, causing distal motion of the burr. Yet a further quarter-rotation results in an attraction. Thus, each rotation of the shaft 20 or 20b results in two back-and-forth motions of the burr, corresponding to a "frequency" doubling. Naturally, the number of magnets may be arranged for no "frequency multiplication," or for multiplication by any appropriate integer. The arrangement of FIGS. 5a and 5b may have any shape of burr, and may have a lumen for a guide wire, as in the case of the other catheters according to the invention.

Figure 6:
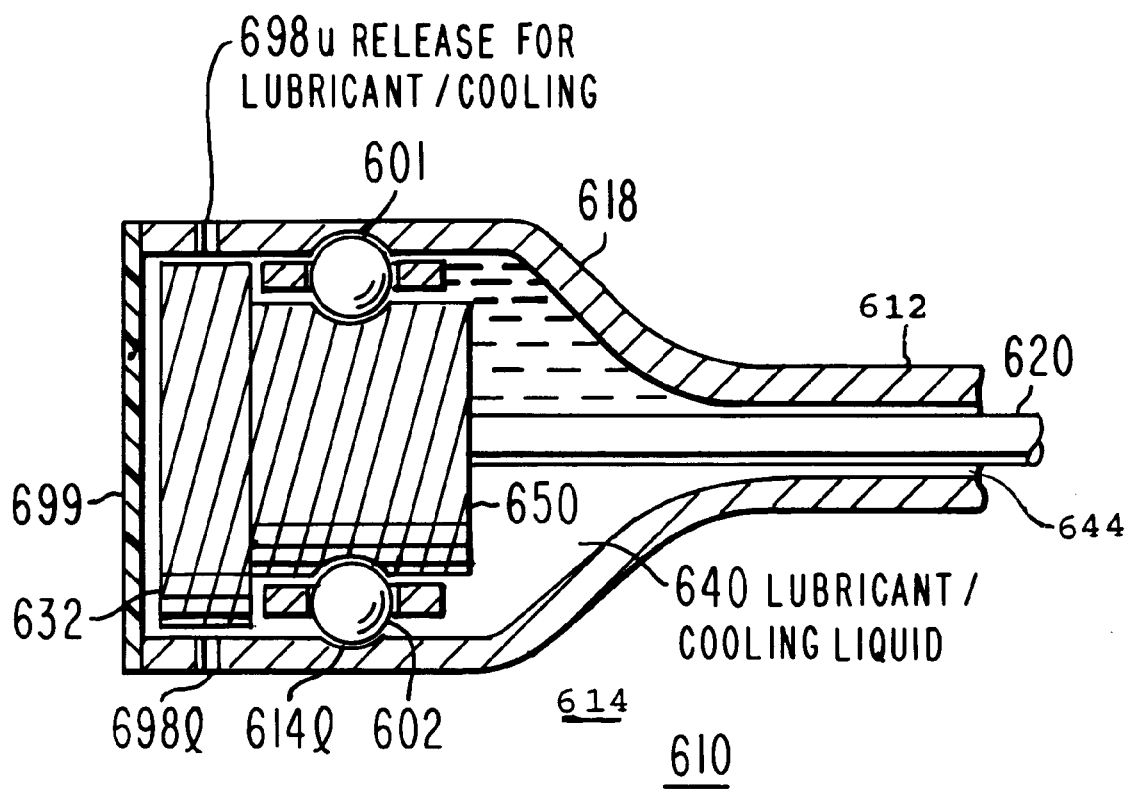
FIG. 6 is a cross-sectional view of the distal end of a catheter according to another embodiment of the invention.

FIG. 6 is a simplified cross-sectional view of another embodiment of the invention, in which acoustical energy is transmitted from the distal end of catheter 610, but no rotational abrasion or cutting is provided. Elements of FIG. 6 corresponding to those of FIG. 3 are designated by similar reference numerals in the 600, rather than the 300 or 00 series. In FIG. 6, distal end 614 of catheter 610 includes a drive shaft 620 which rotates inside a lumen 644 defined within outer wall 612 of the catheter. The distal end of drive shaft 620 is mechanically connected to a disk-like element 650, which is associated with a track defining axial excursions and with track-following ball bearings 601, 602, so that rotation of the shaft 620 results in axial motion of the disk-like element 650. As in the case of the other catheters according to the invention, the acoustic-energy-coupling-surface 632 may be flat as illustrated, or concave, convex, or in any other shape, for tailoring the acoustic energy distribution by focussing or dispersing the energy. An acoustically-transparent membrane 699 covers the open end of cavity 640 within enlarged portion 618 of the catheter. Membrane 699 should have a thickness which is much less than one-half wavelength or λ/2 of the acoustic wave in the biological medium. Also, the acoustic impedance of the membrane 699 should be close to that of the lubricant/coolant liquid, which fills cavity 640 under at least slight pressure, when supplied with fluid under pressure from an arrangement such as that of FIG. 2f. A pair of lubricant/coolant fluid egresses or release openings are illustrated as 698u and 698l in FIG. 6. The distal surface 632 of the disk-like element 650 should be as close as possible to the proximal surface of membrane 699, so as to reduce attenuation losses through the lubricant/coolant fluid filling chamber 640. Membrane 699 may be made from synthetic rubber or plastic materials. The arrangement of FIG. 6 may have a guide-wire lumen as described in relation to FIGS. 2e and 2f, and for allowing distal egress of the guide wire, membrane 699 may have a centered aperture (not illustrated). If membrane 699 has a centered aperture, the lubricant/coolant fluid may leave chamber 640 by way of the centered aperture, as well as by release openings 698u and 698l.

Thus, an acoustic ablation catheter (10) according to the invention is adapted for being driven by a rotary motor (22). The catheter (10) includes an elongated body or housing (12, 18) defining a distal end (14) and a proximal end (16), and a shaft (20) extending at least part-way through the body or housing (12, 18). The shaft (20) is free for rotation and for some axial motion within the housing (12, 18). A rotary coupler (26) is coupled to a proximal (16) end of the shaft (20), for coupling the shaft (20) to the rotary motor (22) for being driven thereby. An axial motion imparting arrangement (46, 56 of FIGS. 2a, 2b, 2c, 2d, and 2g; 301, 302, 311, 312, 314 of FIGS. 3a and 3b; 510, 512 of FIGS. 5a and 5b) located near the distal end (14) of the body (12), and coupled to the shaft (20), causes the shaft (20) to experience axial motion (6) in response to the rotation (4). An acoustic transducer (30) is coupled to a distal end of the shaft (20b) for rotational and axial motion in response to the rotation and axial motion of the shaft. The acoustic transducer (30) is adapted for transferring the axial motion to a biological material or fluid. In a particular embodiment of the invention, the acoustic transducer includes an abrading surface (31) or burr, which can abrade biologic material in response to rotation of the shaft (20). In one embodiment of the invention, a guide-wire lumen (21) extends through the shaft (20) and the applicator or burr (30, 50).

In a particular embodiment of the invention, the axial motion imparting arrangement includes a serrated or toothed surface (56) associated with the shaft (20), bearing on an irregular surface (42 & 46) of the housing (18), together with a position restoring arrangement. In one embodiment of the invention, the position restoring arrangement is a spring arrangement (60) bearing on a portion (24) of the housing (18), for urging the toothed surface (56) toward the irregular surface (42 & 46), which results in rotational motion of the toothed surface (56) against the irregular surface (42 & 46), which in turn results in the axial motion (6) of at least a portion of the shaft (20) near the distal end (14) of the catheter (10). Yet another embodiment has the positions of the spring and of the toothed surfaces reversed. It is not necessary that the toothed surfaces be conical, they may be flat (FIG. 2g).

In another embodiment of the invention, the axial motion imparting arrangement includes a sinusoidal track (314) associated with one of the shaft (20) and the housing (18), and a track following arrangement (301, 302, 310, 311, 312) associated with the other one of the shaft (20) and the housing (18), for imparting sinusoidal axial motion (6) to the shaft. A transducer may be affixed to the axial motion converter.

In another embodiment of the invention, the axial motion imparting arrangement includes magnetic means. The magnetic means may be an array of magnetic poles (510) on one surface which interacts with magnetically influenced means (512) on another surface. In a particular embodiment of the invention, the magnetically influenced means is a further array of magnets.

Other embodiments of the invention will be apparent to those skilled in the art. For example, while burr 30 has been illustrated in two different forms as an applicator of acoustic energy and for cutting, cutter/applicators of other shapes may be used according to the needs of the application. The catheter according to the invention may include other appurtenances which are commonly used with catheters, such as optical fiber scopes, aspiration and medication application lumens, balloons and associated inflation lumens, grasping-type cutters, expanding-balloon medication applicators, and the like. While a "spring" is described for restoring the position of the transducer elements in some of the embodiments, any restoring element can be used. While a rotary coupler in the form of a hollow cylinder 26 has been described, coupling may be accomplished by a welded or brazed connection, adhesives, or any other suitable type of physical connection. The coupling could even be made by means of magnetic, electric or fluid coupling, or anything which couples the desired rotational motion. While ball bearings have been described as track following devices in some embodiments of the invention, it will be clear that other structures can also follow the track, as for example knobs or other projections.

What is claimed is:

1. An acoustic ablation catheter adapted for being driven by a rotary motor, said catheter comprising:

an elongated housing defining a distal end and a proximal end;

a shaft extending at least part-way through said housing, said shaft being free for rotation within said housing, and free for axial motion within at least said distal end of said housing, and rotary coupling means coupled to a proximal end of said shaft, said rotary coupling means being adapted for coupling said shaft to said rotary motor for being driven thereby;

axial motion imparting means located near said distal end of said housing, and coupled to said shaft, for causing at least a portion of said shaft to experience axial motion in response to said rotation; and acoustic transducer means coupled to a distal end of said shaft for rotational and axial motion in response to said rotation and axial motion of said shaft, said acoustic transducer means being adapted for transferring said axial motion to a biological material.

2. An acoustic ablation catheter adapted for being driven by a rotary motor, said catheter comprising:

an elongated housing defining a distal end and a proximal end;

a shaft extending at least part-way through said housing, said shaft being free for rotation within said housing, and free for axial motion within at least said distal end of said housing, and rotary coupling means coupled to a proximal end of said shaft, said rotary coupling means being adapted for coupling said shaft to said rotary motor for being driven thereby;

axial motion imparting means located near said distal end of said housing, and coupled to said shaft, for causing said shaft to experience axial motion in response to said rotation; and acoustic transducer means coupled to a distal end of said shaft for rotational and axial motion in response to said rotation and axial motion of said shaft, said acoustic transducer means being adapted for transferring said axial motion to a biological material;

wherein said axial motion imparting means comprises:

a toothed surface associated with said shaft, bearing on an irregular surface of said housing; and a spring arrangement bearing on a portion of said housing, for urging said toothed surface toward said irregular surface, whereby rotational motion of said toothed surface against said irregular surface results in said axial motion.

3. A catheter according to claim 2, wherein said toothed surface associated with said acoustic transducer means is proximal relative to said spring.

4. A catheter according to claim 2, wherein said toothed surface is distal relative to said spring.

5. A catheter according to claim 2, wherein said acoustic transducer means comprises abrading means for abrading biologic material in response to rotation of said shaft.

6. An acoustic ablation catheter adapted for being driven by a rotary motor, said catheter comprising:

an elongated housing defining a distal end and a proximal end;

a shaft extending at least part-way through said housing, said shaft being free for rotation within said housing, and free for axial motion within at least said distal end of said housing, and rotary coupling means coupled to a proximal end of said shaft, said rotary coupling means being adapted for coupling said shaft to said rotary motor for being driven thereby;

axial motion imparting means located near said distal end of said housing, and coupled to said shaft, for causing said shaft to experience axial motion in response to said rotation; and acoustic transducer means coupled to a distal end of said shaft for rotational and axial motion in response to said rotation and axial motion of said shaft, said acoustic transducer means being adapted for transferring said axial motion to a biological material;

wherein said axial motion imparting means comprises:

a track associated with one of said shaft and said housing, and track following means associated with the other one of said shaft and said housing, for imparting sinusoidal axial motion to said shaft.

7. A catheter according to claim 6, wherein said track following means of said axial motion imparting means further comprises a plurality of balls, kept in position by a like plurality of semispherical hollows associated with said other one of said acoustic transducer means and said housing.

8. A catheter according to claim 7, further comprising a ball cage associated with at least some of said balls, for tending to retain said balls in said hollows.

9. A catheter according to claim 8, wherein said ball cage is fixed to said other one of said acoustic transducer means and said housing.

10. A catheter according to claim 6, wherein said track is associated with said housing, and said track following means is associated with said acoustic transducer means.

11. A catheter according to claim 10, wherein said track following means of said axial motion imparting means further comprises a plurality of balls, kept in position by a like plurality of semispherical hollows associated with said acoustic transducer means.

12. A catheter according to claim 6, wherein said acoustic transducer means comprises abrading means, for abrading biological material in response to rotation of said acoustic transducer means.

13. A catheter according to claim 1, wherein said axial motion imparting means comprises magnetic means coupled to said shaft for rotation thereby, and magnetically influenced means physically coupled to said housing, for at least one of mutual attraction and mutual repulsion between said magnetic means and said magnetically influenced means, in response to rotation of said shaft.

14. A catheter according to claim 13, wherein said acoustic transducer means further comprises abrading means for abrading biological material in response to rotation of said shaft.

15. A catheter according to claim 1, further comprising an elongated axial lumen extending through at least said shaft.

16. A catheter according to claim 15, wherein said axial lumen further extends through at least a part of said acoustic transducer means.

17. A catheter according to claim 16, further comprising a guide-wire inserted at least partially into said lumen of said shaft.

18. A method for performing angioplasty using an acoustic ablation catheter adapted for being driven by a rotary motor, said catheter comprising:

(a) an elongated housing defining a distal end and a proximal end;

(b) a shaft extending at least part-way through said housing, said shaft being free for rotation within said housing, and free for axial motion within at least said distal end of said housing, and rotary coupling means coupled to a proximal end of said shaft, said rotary coupling means being adapted for coupling said shaft to said rotary motor for being driven thereby;

(c) axial motion imparting means located near said distal end of said housing, and coupled to said shaft, for causing at least a portion of said shaft to experience axial motion in response to said rotation; and (d) acoustic transducer means coupled to a distal end of said shaft for rotational and axial motion in response to said rotation and axial motion of said shaft, said acoustic transducer means being adapted for transferring said axial motion to a biological material;

said method comprising the steps of:

if not already so coupled, coupling said shaft to a rotary motor by means of said rotary coupling means;

introducing said distal end of said catheter into a vas in which acoustic ablation is to be performed, and energizing said rotary motor to thereby sonify material contiguous with said acoustic transducer means.

19. A method according to claim 18, wherein said acoustic transducer means of said catheter further comprises abrading means, for abrading biological material in response to rotation of said shaft, and said method comprises the further step of bringing said abrading means into contact with portions of said biological material for abrading said biologic material.

20. A method according to claim 19, wherein a guide-wire lumen extends through said shaft and said acoustic transducer means, and further comprising the step of:

inserting a guidewire through said guide-wire lumen to guide said catheter.

* * * * *